(12) United States Patent
Banouskou

(10) Patent No.: US 9,414,933 B2
(45) Date of Patent: Aug. 16, 2016

(54) EXPANDABLE ORTHOPEDIC DEVICE

(75) Inventor: Ezzine Banouskou, Tournefeuille (FR)

(73) Assignee: Vexim SA, Balma (FR)

( * ) Notice: Subject to any disclaimer, the term of this patent is extended or adjusted under 35 U.S.C. 154(b) by 17 days.

(21) Appl. No.: 14/009,877

(22) PCT Filed: Apr. 7, 2011

(86) PCT No.: PCT/IB2011/001480
§ 371 (c)(1),
(2), (4) Date: Oct. 4, 2013

(87) PCT Pub. No.: WO2012/137031
PCT Pub. Date: Oct. 11, 2012

(65) Prior Publication Data
US 2014/0031940 A1 Jan. 30, 2014

(51) Int. Cl.
A61F 2/44 (2006.01)
A61B 17/88 (2006.01)
A61B 17/70 (2006.01)

(52) U.S. Cl.
CPC ........... *A61F 2/4425* (2013.01); *A61B 17/7065* (2013.01); *A61B 17/8841* (2013.01)

(58) Field of Classification Search
CPC .................... A61F 2002/30579; A61F 2/4611; A61F 2/4455; A61F 2002/30471; A61F 2/442; A61B 17/7068
USPC ............... 623/17.11–17.16; 606/60, 246–249
See application file for complete search history.

(56) References Cited

U.S. PATENT DOCUMENTS

| | | | |
|---|---|---|---|
| 4,796,612 A | 1/1989 | Reese | |
| 4,932,975 A | 6/1990 | Main et al. | |
| 4,961,740 A | 10/1990 | Ray et al. | |
| 4,969,888 A | 11/1990 | Scholten et al. | |
| 5,059,193 A | 10/1991 | Kuslich | |
| 5,108,404 A | 4/1992 | Scholten et al. | |
| 5,665,122 A | 9/1997 | Kambin | |
| 5,693,100 A | 12/1997 | Pisharodi | |
| 5,695,515 A | 12/1997 | Orejola | |
| 5,704,860 A * | 1/1998 | Stief | F16H 7/08 474/110 |
| 5,720,746 A | 2/1998 | Soubeiran | |

(Continued)

FOREIGN PATENT DOCUMENTS

| | | |
|---|---|---|
| CN | 1162349 A | 10/1997 |
| CN | 1713863 A | 12/2005 |

(Continued)

OTHER PUBLICATIONS

French Preliminary Search Report dated Feb. 15, 2005 for French Application No. 0406211.

(Continued)

*Primary Examiner* — Jacqueline Johanas
(74) *Attorney, Agent, or Firm* — Cooley LLP

(57) ABSTRACT

Methods and apparatuses for restoration of human or animal bone anatomy, which may include introduction, into a bone of an expansible implant capable of expansion in a single determined plane, positioning the expansible implant in the bone in order to correspond the single determined plane with a bone restoration plane and opening out the expansible implant in the bone restoration plane. A first support surface and a second support surface spread tissues within bone. The embodiments of the disclosure may also include injecting a filling material around the implant.

29 Claims, 9 Drawing Sheets

(56) References Cited

U.S. PATENT DOCUMENTS

| | | |
|---|---|---|
| 5,800,500 A | 9/1998 | Spelman et al. |
| 5,800,550 A | 9/1998 | Sertich |
| 5,908,448 A | 6/1999 | Roberts et al. |
| 5,972,015 A | 10/1999 | Scribner et al. |
| 5,980,522 A | 11/1999 | Koros et al. |
| 6,039,761 A | 3/2000 | Li et al. |
| 6,066,154 A | 5/2000 | Reiley et al. |
| 6,102,950 A | 8/2000 | Vaccaro |
| 6,126,689 A | 10/2000 | Brett |
| 6,127,597 A | 10/2000 | Beyar et al. |
| 6,176,882 B1 | 1/2001 | Biedermann et al. |
| 6,190,414 B1 | 2/2001 | Young et al. |
| 6,193,757 B1 | 2/2001 | Foley et al. |
| 6,197,033 B1 | 3/2001 | Haid, Jr. et al. |
| 6,214,050 B1 | 4/2001 | Huene |
| 6,235,043 B1 | 5/2001 | Reiley et al. |
| 6,248,110 B1 | 6/2001 | Reiley et al. |
| 6,261,289 B1 | 7/2001 | Levy |
| 6,280,456 B1 | 8/2001 | Scribner et al. |
| 6,332,895 B1 | 12/2001 | Suddaby |
| 6,395,031 B1 | 5/2002 | Foley et al. |
| 6,423,083 B2 | 7/2002 | Reiley et al. |
| 6,454,807 B1 | 9/2002 | Jackson |
| 6,488,710 B2 | 12/2002 | Besselink |
| 6,554,833 B2 | 4/2003 | Levy et al. |
| 6,582,431 B1 | 6/2003 | Ray |
| 6,595,998 B2 | 7/2003 | Johnson et al. |
| 6,607,544 B1 | 8/2003 | Boucher et al. |
| 6,623,505 B2 | 9/2003 | Scribner et al. |
| 6,632,235 B2 | 10/2003 | Weikel et al. |
| 6,663,647 B2 | 12/2003 | Reiley et al. |
| 6,664,897 B2 | 12/2003 | Pape et al. |
| 6,676,665 B2 | 1/2004 | Foley et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,740,093 B2 | 5/2004 | Hochschuler et al. |
| 6,783,530 B1 | 8/2004 | Levy |
| 6,929,647 B2 | 8/2005 | Cohen |
| 6,953,477 B2 | 10/2005 | Berry |
| 6,979,341 B2 | 12/2005 | Scribner et al. |
| 6,981,981 B2 | 1/2006 | Reiley et al. |
| 7,044,954 B2 | 5/2006 | Reiley et al. |
| 7,070,598 B2 | 7/2006 | Lim et al. |
| 7,087,055 B2 | 8/2006 | Lim et al. |
| 7,153,306 B2 | 12/2006 | Ralph et al. |
| 7,217,293 B2 | 5/2007 | Branch, Jr. |
| 7,234,468 B2 | 6/2007 | Johnson et al. |
| 7,241,303 B2 | 7/2007 | Reiss et al. |
| 7,261,720 B2 | 8/2007 | Stevens et al. |
| 7,264,622 B2 | 9/2007 | Michelson |
| 7,318,839 B2 | 1/2008 | Malberg et al. |
| 7,621,950 B1 | 11/2009 | Globerman et al. |
| 7,763,028 B2 | 7/2010 | Lim et al. |
| 7,799,080 B2 | 9/2010 | Doty |
| 7,846,206 B2* | 12/2010 | Oglaza et al. ............ 623/17.11 |
| 7,879,104 B2 | 2/2011 | Dewey et al. |
| 8,282,520 B2* | 10/2012 | Kurematsu ............ F16H 7/0836 474/101 |
| 8,328,818 B1 | 12/2012 | Seifert et al. |
| 8,945,190 B2* | 2/2015 | Culbert et al. ................ 606/279 |
| 8,986,386 B2* | 3/2015 | Oglaza et al. ............... 623/17.15 |
| 2001/0032020 A1 | 10/2001 | Besselink |
| 2002/0065548 A1 | 5/2002 | Birdsall et al. |
| 2002/0120327 A1 | 8/2002 | Cox et al. |
| 2002/0151976 A1 | 10/2002 | Foley et al. |
| 2002/0198532 A1 | 12/2002 | Michelson |
| 2003/0065396 A1 | 4/2003 | Michelson |
| 2003/0074064 A1 | 4/2003 | Gerbec et al. |
| 2003/0171812 A1 | 9/2003 | Grunberg et al. |
| 2003/0220650 A1 | 11/2003 | Major et al. |
| 2003/0236520 A1 | 12/2003 | Lim et al. |
| 2004/0073308 A1 | 4/2004 | Kuslich et al. |
| 2004/0087947 A1 | 5/2004 | Lim et al. |
| 2004/0102774 A1 | 5/2004 | Trieu |
| 2004/0167625 A1 | 8/2004 | Beyar et al. |
| 2004/0210231 A1 | 10/2004 | Boucher et al. |
| 2004/0215343 A1 | 10/2004 | Hochschuler et al. |
| 2005/0107800 A1 | 5/2005 | Frankel et al. |
| 2005/0143827 A1 | 6/2005 | Globerman et al. |
| 2005/0182416 A1 | 8/2005 | Lim et al. |
| 2005/0228391 A1 | 10/2005 | Levy et al. |
| 2005/0273135 A1 | 12/2005 | Chanduszko et al. |
| 2005/0278036 A1* | 12/2005 | Leonard et al. ............ 623/23.47 |
| 2006/0004455 A1* | 1/2006 | Leonard et al. ............ 623/17.15 |
| 2006/0085070 A1 | 4/2006 | Kim |
| 2006/0149379 A1 | 7/2006 | Kuslich et al. |
| 2006/0271049 A1 | 11/2006 | Zucherman et al. |
| 2006/0281595 A1* | 12/2006 | Narita ................... F16H 7/0848 474/109 |
| 2007/0016303 A1 | 1/2007 | Jackson |
| 2007/0021836 A1 | 1/2007 | Doty |
| 2007/0032790 A1 | 2/2007 | Aschmann et al. |
| 2007/0032791 A1 | 2/2007 | Greenhalgh |
| 2007/0142915 A1 | 6/2007 | Altarac et al. |
| 2007/0173826 A1 | 7/2007 | Canaveral et al. |
| 2007/0173939 A1* | 7/2007 | Kim et al. .................. 623/17.11 |
| 2007/0260315 A1 | 11/2007 | Foley et al. |
| 2008/0065087 A1 | 3/2008 | Osorio et al. |
| 2008/0065089 A1 | 3/2008 | Osorio et al. |
| 2008/0086133 A1 | 4/2008 | Kuslich et al. |
| 2008/0114367 A1 | 5/2008 | Meyer |
| 2008/0125784 A1 | 5/2008 | Rabiner et al. |
| 2008/0140079 A1 | 6/2008 | Osorio et al. |
| 2008/0140207 A1 | 6/2008 | Olmos et al. |
| 2008/0147193 A1 | 6/2008 | Matthis et al. |
| 2008/0280712 A1* | 11/2008 | Ryouno ................ F16H 7/0836 474/110 |
| 2009/0228012 A1 | 9/2009 | Gangji et al. |
| 2009/0264927 A1* | 10/2009 | Ginsberg et al. .............. 606/246 |
| 2009/0281628 A1* | 11/2009 | Oglaza et al. ............... 623/17.15 |
| 2010/0070035 A1* | 3/2010 | Mayer ........................ 623/17.16 |
| 2010/0185291 A1* | 7/2010 | Jimenez et al. ............. 623/17.16 |
| 2011/0021298 A1* | 1/2011 | Kurematsu ............ F16H 7/0836 474/110 |
| 2011/0046739 A1* | 2/2011 | Oglaza et al. ............... 623/17.15 |
| 2011/0066186 A1* | 3/2011 | Boyer, Ii et al. .............. 606/249 |
| 2011/0130232 A1* | 6/2011 | Barrette ................ F16H 7/0848 474/101 |
| 2012/0071977 A1* | 3/2012 | Oglaza et al. ............... 623/17.11 |
| 2012/0150228 A1* | 6/2012 | Zappacosta et al. .......... 606/248 |
| 2014/0031940 A1* | 1/2014 | Banouskou ................. 623/17.16 |

FOREIGN PATENT DOCUMENTS

| | | |
|---|---|---|
| CN | 101031259 A | 9/2007 |
| EP | 0796593 A2 | 9/1997 |
| FR | 2782632 A1 | 3/2000 |
| GB | 2435292 A | 8/2007 |
| JP | 2001-173863 | 6/2001 |
| JP | 2006507090 A | 3/2006 |
| JP | 2008501462 A | 1/2008 |
| WO | 9834568 A1 | 8/1998 |
| WO | 9952447 A1 | 10/1999 |
| WO | 0101895 A1 | 1/2001 |
| WO | 0154598 A1 | 8/2001 |
| WO | 0160263 A1 | 8/2001 |
| WO | 0166047 A1 | 9/2001 |
| WO | 03003951 A1 | 1/2003 |
| WO | WO 2004/019756 A2 | 3/2004 |
| WO | 2004026188 A2 | 4/2004 |
| WO | 2004034924 A2 | 4/2004 |
| WO | 2004047689 A1 | 6/2004 |
| WO | 2004086934 A2 | 10/2004 |
| WO | WO 2005/048856 A1 | 6/2005 |
| WO | 2005120400 A2 | 12/2005 |
| WO | 2006068682 A1 | 6/2006 |
| WO | 2006116760 A2 | 11/2006 |
| WO | 2007041665 A2 | 4/2007 |
| WO | 2007073488 A2 | 6/2007 |
| WO | 2007075788 A2 | 7/2007 |
| WO | 2007076308 A2 | 7/2007 |
| WO | 2007076374 A2 | 7/2007 |
| WO | 2007076376 A2 | 7/2007 |

(56) References Cited

FOREIGN PATENT DOCUMENTS

| WO | 2007079237 A2 | 7/2007 |
|---|---|---|
| WO | 2007084239 A2 | 7/2007 |
| WO | 2009125243 A1 | 10/2009 |
| WO | WO 2010/100287 A1 | 9/2010 |
| WO | WO 2010/103344 A1 | 9/2010 |

OTHER PUBLICATIONS

French Preliminary Search Report dated Oct. 28, 2005 for French Application No. 0505798.
International Preliminary Report on Patentability issued Sep. 13, 2011 for PCT/IB2009/005385, filed Mar. 12, 2009.
International Search Report and Written Opinion mailed Dec. 11, 2009 for PCT/IB2009/005385, filed Mar. 12, 2009.
International Preliminary Report on Patentability issued Dec. 14, 2006 for PCT/IB2005/002631, filed Jun. 8, 2005.
International Search Report mailed Feb. 7, 2006 and Written Opinion for PCT/IB2005/002631, filed Jun. 8, 2005.
International Preliminary Report on Patentability issued Oct. 12, 2010 for PCT/IB2008/002246, filed Apr. 8, 2008.
International Search Report mailed on Jan. 29, 2009 for Application No. PCT/IB2008/002246, filed Apr. 8, 2008.
International Search Report mailed Dec. 6, 2011 for PCT/IB2011/001480, filed Apr. 7, 2011.
European Search Report mailed Feb. 22, 2013 for EP Application No. 12191848.6, filed Jun. 8, 2005.
Supplementary Search Report issued on Apr. 8, 2014, by the State Intellectual Property Office of the People's Rep. of China for Application No. 2009801592431, filed Mar. 12, 2009.
International Preliminary Report on Patentability issued Oct. 8, 2013 for PCT/IB2011/001480, filed Apr. 7, 2011.
International Search Report of PCT/IB2011/001480 issued on Dec. 6, 2011.
Japanese Utility Model Application Jikkai Publication No. Sho 62-054313, Apr. 4, 1987 (with partial translation into English).

* cited by examiner

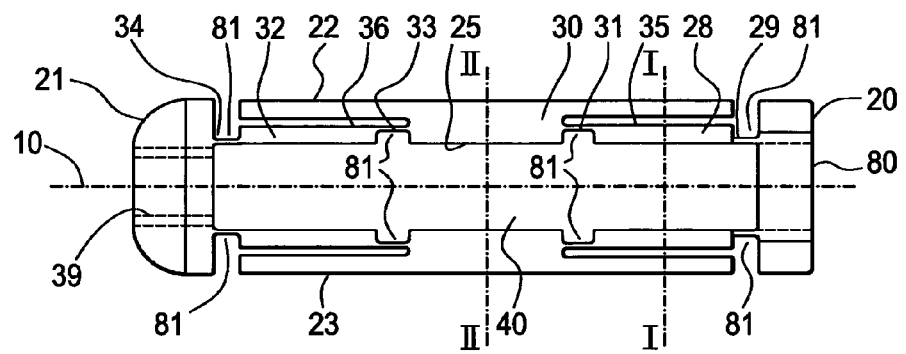
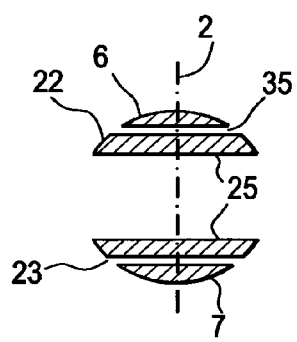
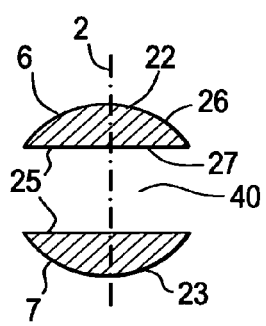
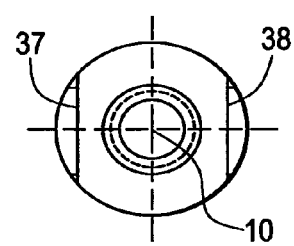
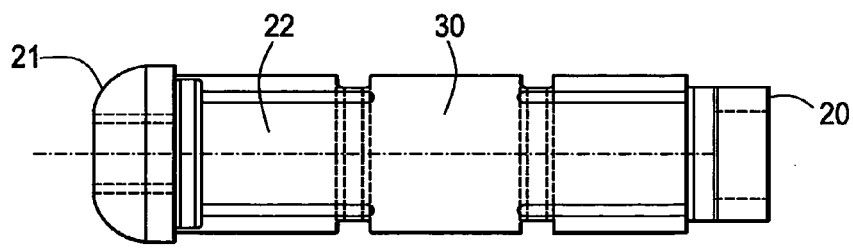

III-III

IV-IV

V-V

VI-VI

EXPANDABLE ORTHOPEDIC DEVICE

CROSS-REFERENCE TO RELATED APPLICATIONS

The present application is a 35 U.S.C. §371 national stage entry of PCT/IB2011/001480, which has an international filing date of Apr. 7, 2011, the disclosure of which is incorporated herein by reference in its entirety.

FIELD OF THE DISCLOSURE

The present disclosure relates to the field of surgery and medical implants and more particularly to devices and methods for restoring human or animal bone anatomy using medical bone implants.

BACKGROUND OF THE DISCLOSURE

Various causes can be at the root of bone compression, in particular osteoporosis which causes (for example) natural vertebral compression under the weight of the individual, but also traumas, with the two causes occasionally being combined. Such bone compressions can affect the vertebrae but also concern other bones, such as the radius and the femur, for example.

Several vertebroplasty techniques are known for effecting a vertebral correction i.e., to restore a vertebra to its original shape, or a shape similar to the latter. For example, one technique includes the introduction of an inflatable balloon into a vertebra, then introducing a fluid under pressure into the balloon in order to force the cortical shell of the vertebra, and in particular the lower and upper vertebral plateaus, to correct the shape of the vertebra under the effect of the pressure. This technique is known by as kyphoplasty. Once the osseous cortical shell has been corrected, the balloon is then deflated, and withdrawn from the vertebra in order to be able to inject a cement into the cortical shell which is intended to impart, sufficient mechanical resistance for the correction to last a significant duration in time.

A notable disadvantage of the kyphoplasty method resides in its numerous manipulations, in particular inflation, and in the necessity to withdraw the balloon from the patient's body. Furthermore, the expansion of a balloon is poorly controlled because the balloon's volume is multi-directional, which often causes a large pressure to be placed on the cortical shell in unsuitable directions. Such large pressures risk bursting of the cortical shell, and in particular, the lateral part of the cortical shell connecting the lower and upper plateaus of a vertebra.

Other vertebral implants exist which are intended to fill a cavity in a vertebra. Such implants, however, generally adopt a radial expansion principle obtained by formation of a plurality of points which stand normally to the longitudinal axis of the implant under the effect of contraction of the latter. Such implants impose too high a pressure on individual points which may pierce the material on which the points support. Furthermore, similar to kyphoplasty, very high pressure can cause bursting of the tissues or organ walls, such as the cortical shell, for example. Furthermore, the radial expansion of some implants does not allow a particular expansion direction to be favoured.

The foregoing description of related art is not intended in any way as an admission that any of the documents described therein, including pending United States patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

SUMMARY OF THE DISCLOSURE

Embodiments of the present disclosure reduce the above noted disadvantages and provide additional advantages over the prior art devices of bone restoration. More particularly, some embodiments of the present disclosure include methods for restoration of human or animal bone anatomy, and include one or more of the following steps: introduction, into a bone for restoring, of an expansible implant according to a single determined expansion plane which is preferably intrinsic to the implant, positioning the expansible implant in the bone in order to make the expansion plane correspond with a bone restoration plane, opening out the expansible implant in the bone restoration plane, and injecting a filling material in an around the implant.

Some of the embodiments of the present disclosure are directed toward an expansible/expandable implant (expansible and expandable being used interchangeably in the present disclosure). The implant may be inserted between two portions of a vertebra, or within an intervertebral space between two vertebrae, for the restoration of the spine (for example). For instance, in some embodiments, the implant may be used to restore and/or expand the distance between two vertebrae (e.g., between two adjacent vertebrae). In some embodiments, the implant may be used as a vertebroplasty device to treat a compression fracture(s) of a vertebral body.

According to some embodiments, a vertebral expandable implant is provided comprising:

at least one bearing surface which expands away from a central longitudinal axis of the implant;

a first implant end and an opposed second implant end, wherein each end includes an opening or recess, and wherein the ends are intended to move toward one another during expansion of the implant;

a retaining member comprising an elongate structure having a first end and second end, wherein each end is configured to engage with a respective opening or recess of each implant end, and wherein at least one end comprises a plurality of ridges and corresponding grooves therebetween; and at least one retaining member engagement member provided within a recess adjacent the first implant end, wherein the engagement member is configured to fit substantially within a groove of the plurality of grooves of the retaining member;

wherein the recess comprises a first end having sufficient depth to allow passage of the engagement member when the engagement member is positioned on a ridge of the retaining member, a second end lacks sufficient depth to allow passage of the engagement member when the engagement member is positioned on a ridge of the retaining member, and wherein the retaining member is configured for retaining the implant in an expanded configuration by substantially preventing contraction of the implant when expanded.

According to some embodiments, methods are provided for retaining an expandable implant in an expanded condition, the said method comprising: introducing into a bone an expansible implant, said implant comprises at least one bearing surface which expands away from a central longitudinal axis of the implant; and a first implant end and an opposed second implant end, wherein the ends are intended to move toward one another during expansion of the implant, and wherein each end includes an opening or retaining recess, said retaining recess housing an engagement member;

expanding the implant such that the implant engages a mechanical resistance configured to prevent the compression of the implant, wherein said mechanical resistance is placed between the first implant end and the opposed second implant end;

the mechanical resistance comprising a retaining member comprising an elongate structure having a first end and second end, wherein at least one end comprises a plurality of ridges and corresponding grooves therebetween, and wherein the at least one end is configured to engage a respective opening or retaining recess of at least one implant end;

positioning the retaining member such that the engagement member engages at least one groove of the retaining member, wherein the engagement member is configured to fit substantially within a groove of the plurality of grooves of the retaining member;

wherein the retaining recess is configured to permit passage of the engagement element over the ridges of the retaining element during expansion on the implant, and wherein the retaining recess is configured to block passage of the engagement element over a ridge of the retaining element upon application of a compression force to the implant, thereby retaining the engagement element in a groove of the retaining member, and thereby retaining the implant in an expanded configuration by substantially preventing contraction of the implant when expanded.

According to some embodiments, a vertebral expandable implant is provided comprising an implant, a retaining member, and a retaining member placement engagement member;

wherein the implant comprises first and second opposed bearing surfaces wherein the first and second opposed bearing surfaces move away from one another according to a plane of expansion during expansion of the implant;

wherein the implant further comprises a distal and proximal opposed ends associated with each of the bearing surfaces intended to move toward one another during expansion of the implant;

wherein the retaining member is an elongate member with a first end and second end, wherein at least one end comprises a plurality of ridges and grooves, wherein the engagement member is configured to fit within a groove of the plurality of grooves.

wherein the first and second opposed ends of the implant comprise an aperture configured for receiving the retaining member, wherein at least one end comprises a recess housing the engagement member, wherein the recess comprises a first end and a second end, wherein the first end has sufficient depth to allow free passage of the engagement member when the engagement member is positioned on a ridge of the retaining member, and wherein the second end of the recess lacks sufficient depth to allow free passage of the engagement member when the engagement member is positioned on a ridge of the retaining member; and wherein the retaining member is configured for retaining the implant in an expanded configuration by blocking the contraction of the expanded implant.

The plurality of ridges and grooves may completely or partially circumscribe the outer surface of the retaining member.

The plurality of grooves may extend inward away from the outer surface of the retaining element, wherein upon expansion of the implant, an engagement member (e.g., circlips) moves between ridges and grooves during the passage of the retaining member.

The expansion of the implant comprises movement of at least one of the end members relative to the retaining element.

In some embodiments, the retaining element is tubular and the one or more recesses at least partially circumscribe the outer surface of the retaining member. In some embodiments, the retaining element is tubular and comprises a lumen configured for allowing the passage of a flowable material therethrough. The retaining element may further comprises an aperture configured for allowing the egress of the flowable material from the lumen of the tubular retaining element. The flowable material may comprise a bone cement or bone graft.

In some embodiments, the at least one of the end members is configured for association with an implant expander. The implant expander may comprises a proximal portion and a distal portion, wherein the distal portion is configured for association with at least one of the end members of the implant. The proximal portion of the implant expander may be configured for being coupled to an injection member of an injection system. The proximal portion may comprises a luer lock, threaded, or bayonet configuration.

According to some embodiments, an expansible implant is provided for bone restoration comprising: a single plane of expansion intrinsic to the implant, wherein the single plane of expansion corresponds to a bone restoration plane; first and second opposed plates respectively forming first and a second bearing surfaces for the bone, wherein the first and second plates move away from one another according to the single plane of expansion at the time of the expansion of the implant; first and second implant ends substantially aligned along a longitudinal axis of the implant, wherein the first implant end includes an opening for allowing engagement of the implant with an implant carrier; at least one pair of first and second supports, wherein each support of a pair of supports includes a first end connected to the first or second plate and a second end connected to the first or second implant ends; and a first material web provided between each respective support and the corresponding plate the support is connected to, and a second material web provided between each respective support and the corresponding implant end the support is connected to, wherein each material web plastically deforms during expansion of the implant to control expansion of the implant, and wherein each material web comprises a reduced thickness portion of a respective support.

According to some embodiments, methods are provided for restoration of human or animal bone anatomy (e.g., vertebra), comprising: introducing, into a bone, an expansible implant according to the present embodiments. In some embodiments, methods are provided for restoration of human or animal bone anatomy, comprising: introducing, into a bone, an expansible implant having: at least one bearing surface which expands away from a central longitudinal axis of the implant; a first implant end and an opposed second implant end, wherein each end includes an opening or recess, and wherein the ends are intended to move toward one another during expansion of the implant; a retaining member comprising an elongate structure having a first end and second end, wherein each end is configured to engage with a respective opening or recess of each implant end, and wherein at least one end comprises a plurality of ridges and corresponding grooves therebetween; and at least one retaining member engagement member provided within a recess adjacent the first implant end, wherein the engagement member is configured to fit substantially within a groove of the plurality of grooves of the retaining member; wherein the recess comprises a first end having sufficient depth to allow passage of the engagement member when the engagement member is positioned on a ridge of the retaining member, a second end lacks sufficient depth to allow passage of the engagement member when the engagement member is positioned on a ridge of the retaining member, and wherein the retaining member is configured for retaining the implant in an expanded configuration by substantially preventing contraction of the implant when expanded.

According to some embodiments, methods are provided for restoration of human or animal bone anatomy, comprising: introducing, into a bone, an expansible implant having: a single plane of expansion; at least one plate forming a bearing surface for bone, wherein upon expansion of the implant, the plate is directed away from a longitudinal axis of the implant according to the single plane of expansion at the time of the expansion of the implant; first and second implant ends substantially aligned along the longitudinal axis of the implant, wherein the first implant end includes an opening for allowing engagement of the implant with an implant carrier; at least one support connected to at least one plate and at least one implant end; and a zone of material provided between the at least one support and at least one of the at least one plate and the at least one implant end, wherein the zone of material plastically deforms during expansion of the implant for controlling the expansion of the implant, and wherein the zone of material comprises a reduced thickness portion of a respective support; positioning the expansible implant in the bone in order to correspond the single plane of expansion with a bone restoration plane, and expanding the implant in the bone restoration plane.

According to some embodiments, an expansible implant may comprise a retaining member.

BRIEF DESCRIPTION OF THE DRAWINGS

For a better understanding of the present disclosure, reference is made to the following description, taken in conjunction with the accompanying drawings, in which like reference characters refer to like parts throughout.

FIG. 3 illustrates a lateral view of the example according to FIG. 1A.

FIG. 4 illustrates a view in section according to the line I-I of FIG. 3.

FIG. 5 illustrates a view in section according to the line II-II of FIG. 3.

FIG. 6 represents an end view according to view F of the example according to FIG. 1A.

FIG. 7 illustrates a view from above of the example according to FIG. 1A.

DETAILED DESCRIPTION

Figure 1A:
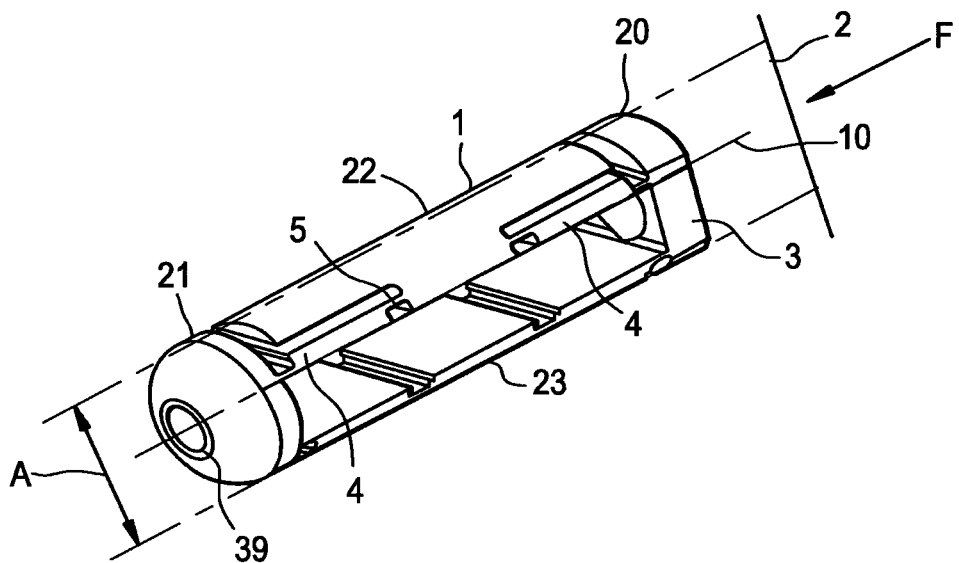
FIG. 1A illustrates a perspective view of one embodiment of an expansible implant according to the disclosure, in a resting position.

In the following description of the preferred embodiment, reference is made to the accompanying drawings which form a part hereof, and in which is shown by way of illustration a specific embodiment in which the disclosure may be practiced. It is to be understood that other embodiments may be utilized and structural changes may be made without departing from the scope of the present disclosure.

The method, according to some embodiments of the disclosure, allows the creation of a reinforced structure resulting in a solid structure (i.e., the implant incorporated by a hardened filling material thanks to the expansion of the implant). Moreover, the filling material can be injected under relatively low pressure since the implant remains in place which enables the preservation of the dimensions of the corrected bone structure.

It is another feature of an embodiment of the present disclosure that the expansible implant may be expanded/opened-out in the bone restoration plane to a determined value: between a minimum thickness of the implant before any expansion and a maximum thickness of the implant after maximum expansion. Such a feature allows the expansion value of the implant to be controlled, for example, for a given vertebral correction.

Another advantageous feature of an embodiment of the present disclosure includes the opening out of the expansible implant by opening out first and second opposite plates, forming (respectively) first and a second support surfaces for the bone. Such a feature allows the pressure which is exerted by the implant on the tissues in contact with the latter to be reduced, by increasing the contact or support surface on the tissues.

The length of the implant may also be sized to be substantially equal to at least one of the first and second support surfaces in the bone. Such a feature allows optimization of a ratio of the support length on the tissues to the length of the implant. For example, the closer this ratio is to one, the more the implant will be usable in places requiring a small length. Moreover, this feature also allows the introduction of a filling material with low injection pressure—in one embodiment, the injection pressure is the lowest possible so as to avoid having the filling material be injected into inappropriate tissues such as blood vessel walls (for example).

In another embodiment of the disclosure, each of the first and second plates may form partially cylindrical support surfaces, one portion of which may be parallel to a longitudinal axis of the expansible implant.

In another embodiment of the present disclosure, the opening out of first and second plates includes raising the latter using one or more supports under the plates. Such a feature allows a ratio of the length of the support surfaces to the length of the implant to be increased to be as close to one (1) as possible, as will be explained in more detail further on with the description of an embodiment of the disclosure. Furthermore, this feature allows thrust forces to be distributed under the plate in order to reduce the cantilever.

A filler cement may be injected in an around the implant, so as to aid in compressive load with the implant in bone restoration. Cements that may be used with the implants according to the disclosed embodiments may include an ionic cement, in particular a phosphocalcic cement, an acrylic cement or a compound of the latter. Accordingly, the combination of the implant and the cement is not unlike a steel reinforced concrete structure in the construction of buildings.

In one embodiment of the present disclosure, an expansible implant for bone restoration is presented and may include a single plane of expansion intrinsic to the implant, where upon the single plane of expansion corresponds to a bone restoration plane and first and second opposed plates respectively form first and a second bearing surfaces for the bone. The first and second plates are intended to move away one from the other according to the single plane of expansion at the time of the expansion of the implant. The implant may also include first and second supports for each of the first and second bearing surfaces, located under each plate respectively and means for controlling expansion of the implant. The controlling means may include a material web provided between each support and a corresponding plate, having a determined thickness which controls expansion of the implant. Moreover, one or more implants may be used in a single bone to produce a more symmetrical bone restoration.

Accordingly, additional embodiments of the present disclosure may also include control means for controlling a determined expansion value, between a minimum thickness of the implant before any expansion of the latter and a maximum thickness of the implant after its maximum expansion.

The implant may also preferably include a means for positioning the expansible implant in bone in order to make the expansion plane of the implant correspond substantially with a bone restoration plane. Such means may include an engagement means allowing angular orientation of the implant about the longitudinal axis, including flat surfaces for attachment with an implant carrier, and threaded engagement.

Another embodiment of the disclosure is directed to a system for bone restoration and may include at least one expansible implant having a single plane of expansion for corresponding to a bone restoration plane, a first tube for positioning adjacent an exterior surface of a bone for restoration, and a first rod having a threaded end for affixing into a distal end of the interior of the bone, where the first rod being received within the first tube. The system may also include a second tube for receiving the first tube therein and a third tube for receiving the second tube, where the third tube including one or more engagement members for anchoring the third tube on the exterior surface of the bone. The system may further include a drill for establishing an enlarged opening in the side of the bone, where the drill is guided by the first rod and a medical insertion device for inserting an expansible implant into a patient.

Another embodiment of the disclosure is directed to a medical insertion device for inserting an expansible implant into a patient. The device may include a gripping portion having a central bore, a first tube housed in the central bore, a threaded rod housed in the first tube having a distal end for receiving an implant for insertion into the patient, a handle attached to the gripping portion and/or the implant carrier and a gauge for determining an expansion of the implant.

The expansible implant 1 represented in FIGS. 1A to 7 may include one or more of the following: a single determined expansion plane 2, which may be intrinsic to the implant, means 3 for positioning the expansible implant in the bone allowing the expansion plane to correspond with a bone restoration plane, means 4 for opening out the expansible implant in the single expansion plane 2, means 5 for controlling a determined expansion value, between a minimum thickness A of the implant before any expansion of the latter and a maximum thickness B of the implant after its maximum expansion, and a first 6 and a second 7 opposite plate which are able to form respectively a first 8 and a second 9 support surface in the bone intended to be moved apart one from the other along the single expansion plane 2 during expansion of the implant 1.

Figure 1B:
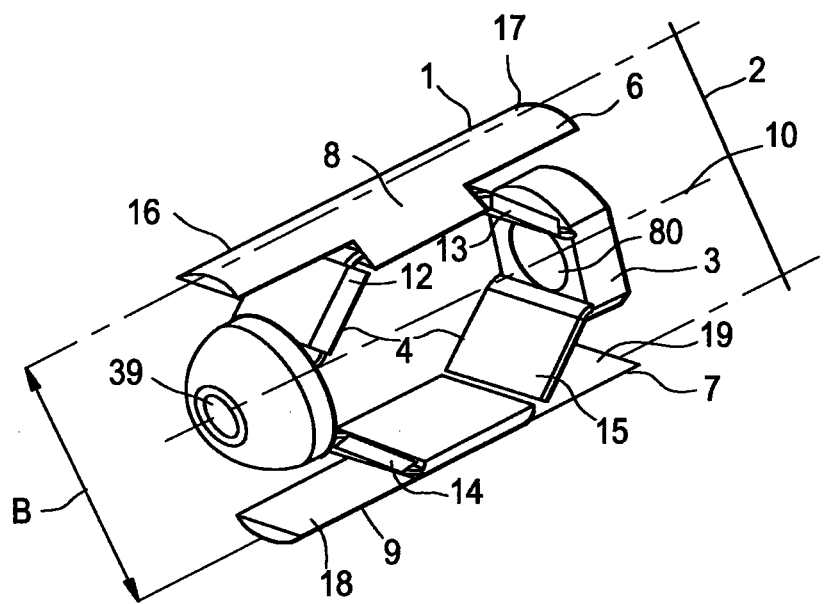
FIG. 1B illustrates the example of FIG. 1A, in opened-out position.

As shown in FIGS. 1A and 1B, implant 1 may include a cylindrical shape with a transverse circular exterior section, and can be manufactured of biocompatible material, for example titanium, into a tubular body using lathe, laser, and/or electro-erosion manufacturing techniques (cast manufacturing may also be used). The implant 1 may also include a first end 20 and a second end 21, each respectfully adopting the shape of a transverse section of the tubular body. The ends are preferably intended to be brought towards one another to allow the opening-out/expansion of the implant, as represented in FIGS. 1B and 2B. Accordingly, the two ends 20, 21 are connected to each other by a first 22 (which also may be referred to as "upper" arm) and second 23 (which also may be referred to as "lower" arm) rectilinear arm, which are parallel when the implant is not opened out and formed longitudinally in the tubular body, and are able to be folded under the first 6 and second 7 opposite plates as an effect of bringing the ends 20 and 21 one towards the other, while also distancing the first 6 and second 7 opposite plates from the longitudinal axis 10 of the tubular body.

Figure 2A:
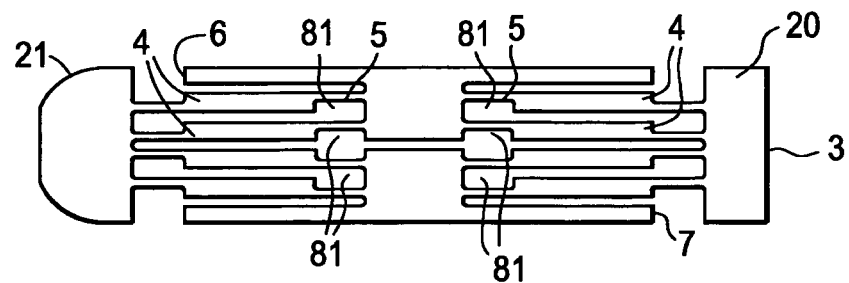
FIG. 2A illustrates a side view of another embodiment of an expansible implant according to the disclosure, in a resting position.
Figure 2B:
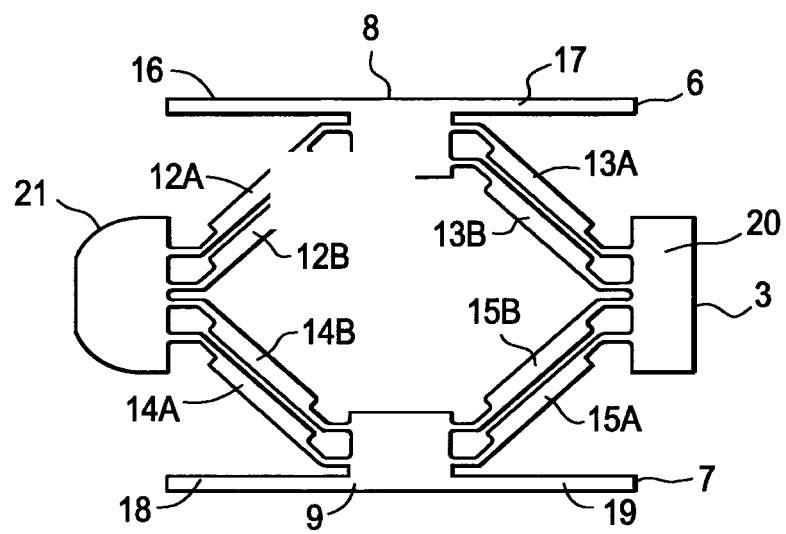
FIG. 2B illustrates the example of FIG. 2A, in opened-out position.
Figure 2C:
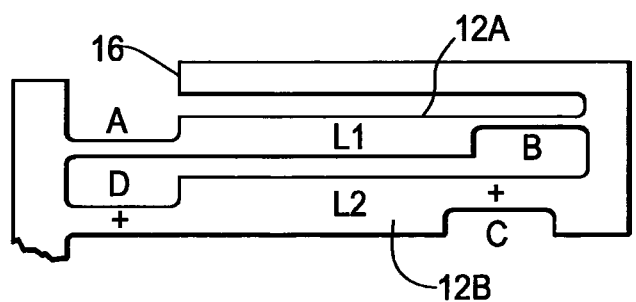
FIG. 2C illustrates an enlarged side view of the support members for the embodiment illustrated in FIGS. 2A and 2B.

FIGS. 2A-2C illustrate an embodiment of the implant which is similar to the embodiment disclosed in FIGS. 1A and 1B, but with an additional set of supports (e.g., a four bar linkage). More specifically, the implant in FIGS. 2A-2C includes supports 12A, 12B, 13A, 13B, 14A, 14B, 15A, and 15B. The additional supports may provide further rigidity for the implant and/or may insure that plates 6 and 7 open-out in a substantially parallel and/or even manner.

As represented in FIGS. 4-5, in order to allow the arms 22 and 23 to be opened out in a single expansion plane 2 (passing through the longitudinal axis 10 of the tubular body), the arms 22 and 23 are preferably diametrically opposed. In that regard, the arms 22, 23 may be formed from a transverse recess 40 of the tubular body, traversing the tubular body throughout, and extending over the length of the tubular body between the two ends 20 and 21 of the implant 1. As represented in FIG. 5, the arms, 22, 23 connecting the two ends 20 and 21, respectively adopt a transverse section bounded by a circular arc 26 of the exterior surface of the tubular body. Chord 27 defines the circular arc 26 and may be included in the wall 25 to form recess 40. The recess 40 may be symmetrical with respect to the longitudinal axis 10.

Each arm 22, 23 may be divided into three successive rigid parts, which may be articulated together in conjunction with the ends 20 and 21 as follows. With respect to the upper arm 22: a first rigid part 28 is connected at one end to end 20 by means of an articulation 29. The other end of rigid part 28 is connected to a first end of a second, adjacent, central rigid part 30 by means of an articulation 31. The second rigid part 30 may be connected at a second end to the third rigid part 32 by means of an articulation 33. The other end of the third rigid part 32 may be connected to end 21 by means of an articulation 34. Preferably, the articulations 29, 31, 33 and 34 may include one degree of freedom in rotation, acting, respectively, about axes which are perpendicular to the expansion plane 2. Preferably, articulations 29, 31, 33 and 34 are formed by a thinning of the wall forming the arm in the relevant articulation zone, as represented in FIGS. 1A-3 (see also, e.g., reference numerals 5 and 81).

Each arm 22, 23 opens out such that the central rigid part 30 moves away from the longitudinal axis 10 of the implant pushed by the two adjacent rigid parts 28 and 32, when the ends 20 and 21 of the implant are brought one towards the other. As represented more particularly in FIG. 3, in order to initiate the movement of the arm in the correct direction when the ends 20 and 21 are brought towards the other, it is preferable to establish a suitable rotation couple of the various parts of the arm.

Accordingly, ends of rigid parts 28, 32 of upper arm 22 may be articulated with ends 20 and 21, respectively, via a material web formed on the rigid parts. Other ends of rigid parts 28, 32 may also be articulated with the central rigid part 30 via a material web formed on rigid parts 28, 32. The displacement of the articulations establish a rotation couple on the rigid parts 28 and 32 when a force is applied to bring the ends 20 and 21 together along the longitudinal axis 10 of the implant. This displacement tends to make the rigid part 32 pivot towards the exterior of the implant as a result of moving the central rigid part 30 away from the longitudinal axis 10.

The lower arm 23 may be constructed in a similar manner as the upper arm and is preferably symmetrical to the upper arm 22 with respect to a plane which is perpendicular to the expansion plane 2 passing through the longitudinal axis 10.

Thus, according to some embodiments of the present disclosure, the articulations between the upper 22 and lower 23 arms and corresponding rigid parts are preferably formed by weakened zones produced by grooves 81. The grooves define a thin web of material (i.e., material web) formed from the tubular body, the thickness of which may be determined by the depth of the grooves 81 (as represented in the figures) in order to allow plastic deformation of the material without breaking. Specifically, the rigid parts 28 and 32 of the upper arm 22, and their symmetrical ones on the lower arm 23, can adopt a position, termed extreme expansion, in which the intended rigid parts are perpendicular to the longitudinal axis 10 of the implant 1, when the ends 20 and 21 are brought one towards the other such that the latter is opened up until its maximum expansion capacity, resulting in plastic deformation of the corresponding material. The width of the grooves 81 are preferably pre-determined to allow such a clearance of the parts of the upper and lower arms and also to impart a suitable radius of curvature to the webs in order to ensure plastic deformation without rupture of the material.

The first 6 and second 7 opposite plates may be formed in the upper 22 and lower 23 arms. With respect to the upper arm 22, for example, plate 6 may be formed by the central rigid part 30 and by material extensions (rigid parts 28 and 32) extending out both sides thereof. In order to produce the plate 6, rigid parts 28 and 32 are separated from the upper arm 22 using a pair of transverse slots 35 and 36 which extend longitudinally over the length each respective end part (see FIGS. 3-4). Articulations 31 and 33 and rigid parts 28 and 32 form, respectively, a first 12 and a second 13 support (FIG. 1B) for the first 6 plate. The same applies to the second plate 7 by symmetry.

Hence, the first 6 and second 7 plates may comprise respectively a first 16, 18 and a second 17, 19 cantilever wing, the respective attachment zones of which are situated at the level of the first 12, 14 and second 13, 15 supports. As represented in FIGS. 1A-B, the first 16, 18 and second 17, 19 cantilever wings may include a length corresponding substantially to the maximum displacement value of one of the first 6 or second 7 plates in the single expansion plane 2.

The first 6 and second 7 plates form first 8 and second 9 support surfaces, respectively, each having a length which may be substantially equal to the length of the implant and which may be displaced perpendicularly to the longitudinal axis 10 during expansion. According to one embodiment of the disclosure, since the implant 1 is formed in a tubular body, the first 6 and second 7 plates form, respectively, curved support surfaces, which are preferably parallel to the longitudinal axis 10.

The means 3 for positioning the expansible implant in a bone which allow the expansion plane 2 to correspond with a bone restoration plane, may include an engagement means which allows for the angular orientation of the implant about longitudinal axis 10. For example, such means may include flat surfaces 37, 38 which are formed on the cylindrical surface with a circular section of end 20, which may allow for rotational engagement of the implant 1.

The means 4 for opening out the expansible implant in a single expansion plane 2, may include rigid parts 28 and 32 of upper arm 22 and the corresponding symmetrical rigid parts on the lower arm 23, allowing opening out of the first 6 and second 7 plates. An implant carrier 71 (see FIG. 23) may be used to allow the ends 20 and 21 of the implant to be brought together when placed within the bone. The implant carrier 71, by being supported on the end 20, for example, allows the end 21 to be pulled toward end 20, or by being supported on end 21, end 20 is pushed toward end 21. To this end, the distal end 21, for example, comprises an opening/distal orifice 39 threaded along the longitudinal axis 10 in order to allow the engagement of the implant carrier 71, which includes a corresponding threaded portion. The proximal end 20 may include a bore 80 along the longitudinal axis 10 in order to allow the passage of a core of the implant carrier 71 as will be explained further on.

A control means may be provided by the implant carrier which may include a millimetric control means for bringing ends 20 and 21 together, preferably by means of screw-thread engagement, allowing the expansion to be stopped at any moment as a function of requirements. On the other hand, control means 5 provided by the articulations of the arms 22 and 23, more specifically, by the thickness of the material webs defining each arm which, deforming in the plastic region, allow the expansion to substantially preserve a determined opening-up position of the arms, apart from elastic shrinkage which is negligible in practice.

The expansion of the plates 6 and 7 of the implant, and their stabilisation once opened up, can be achieved through adaptation of plates 6 and 7 to the bone geometry by the plates. Specifically, in some embodiments of the disclosure, the implant 1 allows a non-parallel displacement of plates 6 and 7 and, at the end of the displacement, allows a definitive position of the plates in a non-parallel state if necessary (e.g., as a function of the bone anatomy). For example, the expansion of plates 6 and 7 may be non-parallel if the lengths of individual support arms are different. For example, if supports 12 and 14 are longer than supports 13 and 15 (see FIGS. 1A-2B), opening out the implant will force plates 6 and 7 to angle away from each other. In FIGS. 1A-2B, this would result that plates 6 and 7 at end 21 to be further apart one another then at end 20. As one of ordinary skill in the art will appreciate, depending upon the configuration, only one respective support need be lengthened/shortened, to obtain a particular angle.

Similarly, as shown in FIGS. 2A-2C, when the four bar linkage comprising supports 12A, 12B, 13A, 13B, 14A, 14B, 15A, 15B, as shown, are equal lengths (i.e., length of 12A=length of 13A, length of 12B=length of 13B, etc.), a parallelogram is then created upon expansion of the implant, which insure parallelism between segments AD and BC (FIG. 2C). By modifying the lengths of L1 and L2, the four bar linkage is no longer a parallelogram, but rather an angle between plate 6 and 7 occurs. The angle formed may also be dependent on how close ends 20 and 21 are drawn near to each other. As the implant is opened-out, the angle slowly increases.

FIGS. 8-16 relate to a second embodiment of an expansible implant 101, the elements of which are functionally similar to the corresponding elements of the implant embodiment illustrated in FIGS. 1-7. Moreover, the corresponding features in FIGS. 8-16 relating to the embodiment illustrated in FIGS. 1-7 include the same reference numerals, respectively, with the addition of the number 100 and therefore will not be described further.

Figure 9:
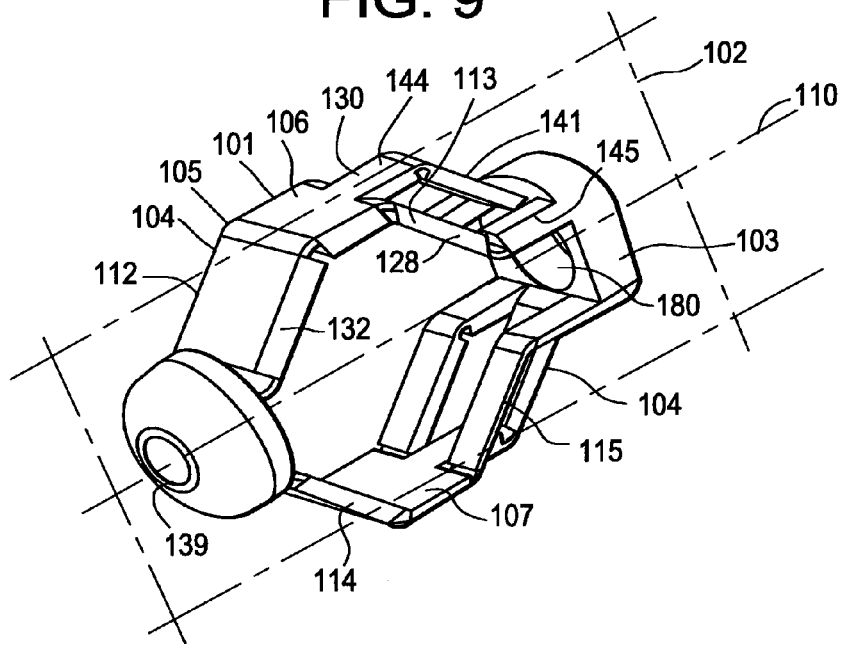
FIG. 9 illustrates the example of FIG. 8, in opened-out position.
Figure 10:
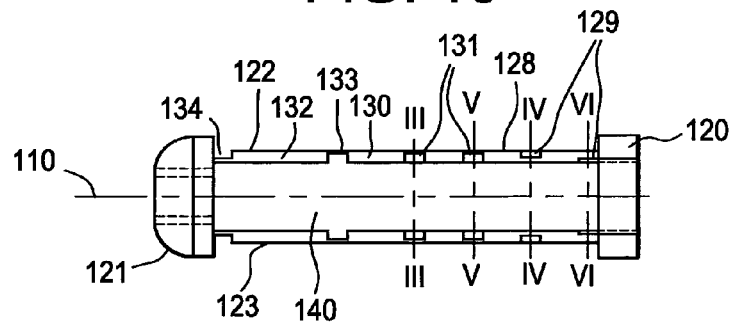
FIG. 10 illustrates a lateral view of the example according to FIG. 8.
Figure 11:
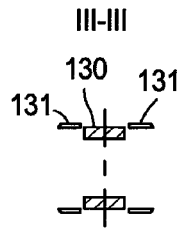
FIG. 11 illustrates a view in section according to the line of FIG. 10.
Figure 12:
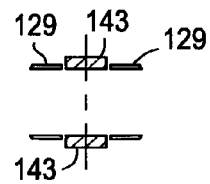
FIG. 12 illustrates a view in section according to the line IV-IV of FIG. 10.
Figure 13:
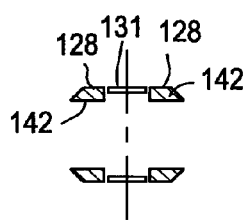
FIG. 13 illustrates a view in section according to the line V-V of FIG. 10.
Figure 14:
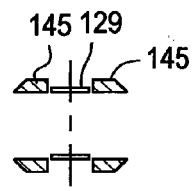
FIG. 14 illustrates a view in section according to the line VI-VI of FIG. 10.
Figure 15:
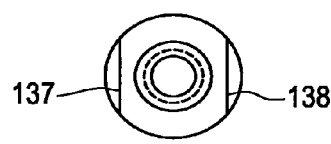
FIG. 15 illustrates an end view according to direction G of the example according to FIG. 8.
Figure 16:
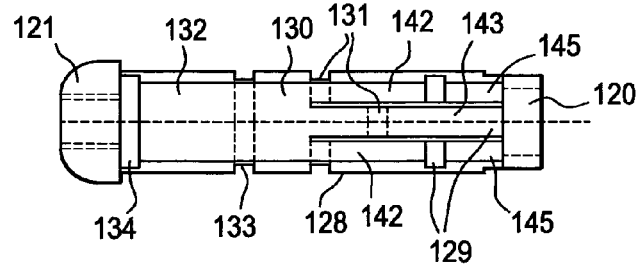
FIG. 16 illustrates a view from above of the example according to FIG. 8.

The represented implant 101 differs from the implant 1 by the absence of the wing portion on the plates 106 and 107, as represented more particularly in FIG. 9. Implant 101 includes a deformable parallelogram system 141 on one of the rigid parts 128 or 132 of each of the arms 122 (upper) and 123 (lower). In the illustrated example, the parallelogram system is represented on rigid part 128 of upper arm 122, connected to the end 120 and the corresponding system on lower arm 123. The parallelogram systems may be used to ensure displacement of the plates of each of the arms 122 and 123, parallel to longitudinal axis 110 of the implant. As represented in the figures, the rigid part 128 of the arm 122 (similarly on corresponding arm 123) is split, as are articulations 131 and 129 (respectively) over the central part 130 and over the end 120 of the implant in order to form a parallelogram which is deformable during displacement of the corresponding plate.

The articulations of the deformable parallelogram 141 may be produced in the same manner as the other articulations 131, 133, 134 of the arm 122, as represented in FIGS. 8-16. The disclosed geometry as explained above and represented in FIGS. 11-14, establishes force couples on the various parts 129, 130, 132 of the arm. This allows for the desired displacements when bringing together ends 120 and 121 of the implant 101.

In order to obtain a deformable parallelogram 141, the rigid part 128 of the arm is preferably divided into three longitudinal levers: two lateral levers 142 and a central lever 143, which form two sides of the deformable parallelogram 141.

Figure 8:
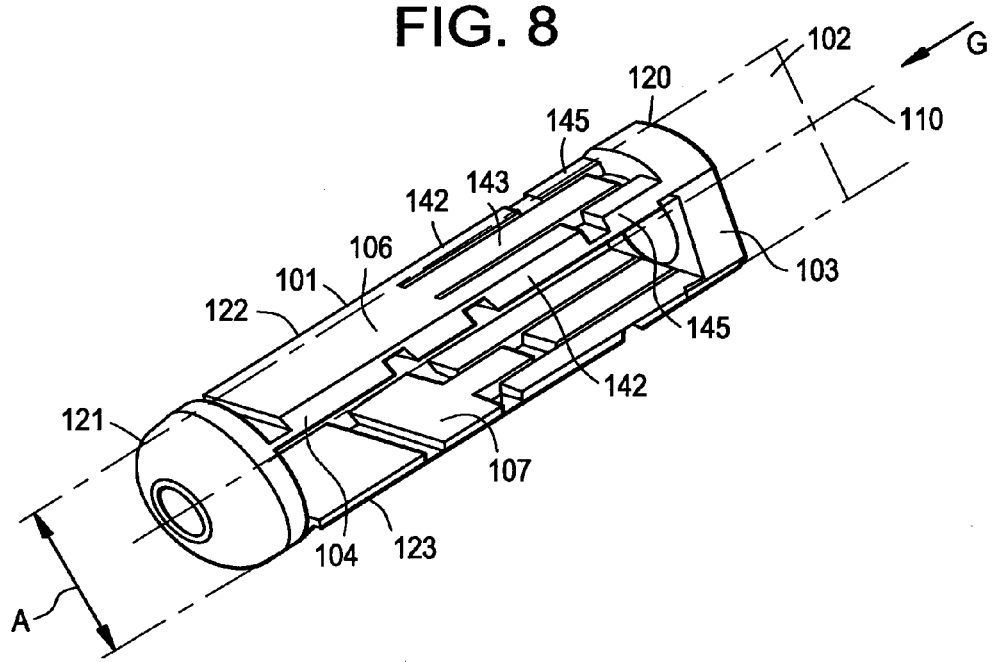
FIG. 8 illustrates a perspective view of another embodiment of an expansible implant according to the disclosure, in a resting position.

The two remaining sides of the parallelogram may be formed by an extension 144 of the central part of the arm 122, placed in an axis of extension of the central lever 143, and by a double extension 145 of the end 120, extending parallel to the longitudinal axis 110 of the implant and placed in the axis of extension of the two lateral levers 142 (see FIG. 8).

It is worth noting that arms 122 and 123 may be symmetrical with respect to a plane which is substantially perpendicular to the plane of expansion 102 passing through the longitudinal axis 110 of the implant 101 in order to obtain, during the expansion of the implant, the displacement of the two plates 106 and 107 in a manner parallel to the longitudinal axis 110.

Bone Restoration

The expansible implant of the present embodiments may be used in methods for human bone restoration as is described in U.S. Pat. No. 7,846,206, incorporated herein by reference in its entirety.

Retaining Member

Some embodiments of the subject disclosure are directed toward a vertebral expandable implant which comprises first and second bearing surfaces intended to move away from one another during expansion of the implant, at least first and second opposed ends associated with each of the bearing surfaces, and a retaining member for retaining the implant in an expanded configuration. In some embodiments, the retaining element has an elongate body that has a diameter that ranges from about 1 mm and about 6 mm for instance, between about 2 mm and about 5 mm, such as between about 3 mm and about 4 mm. In some embodiments, the elongate body of the retaining element may have a length that ranges from about 10 mm and about 45 mm, for instance, about 15 mm and about 30 mm or about 25 mm, such as about 18 mm and about 20 mm.

In some embodiments, the retaining member also functions as a rigid beam between the two end members 20, 21 that maintains the implant in proper form and manages the opening of the implant to ensure proper expansion (e.g., protects the implant from bending or becoming deformed).

According to some embodiments, the retaining element comprises a mechanical resistance. The mechanical resistance may include an engagement element (e.g., circlip) and an engagement element receiving member (e.g., blocking steps). In certain instances, the engagement element and the receiving member may be configured for associating with one another in such a manner so as to restrain the implant from contracting once expanded. The receiving member may be positioned on the retaining member, and in this manner, the engagement element acts as a retaining member placement mechanism.

Further, due in part to the mechanical resistance of the subject implant, the implant may have a variety of configurations that range between a minimally collapsed configuration to a maximally expanded configuration. For instance, the mechanical resistance may be such that it includes a plurality of resistance elements configured for allowing the expansible implant to expand to one or more designated heights. For example, the mechanical resistance may include a plurality of ridges, notches, and engagement elements as well as engagement element receiving members. In this manner, the degree and rate of expansion of the implant may be precisely controlled by the configuration and placement of the mechanical resistance elements so as to allow the implant to be expanded in such a way as to specifically conform to an inter-vertebral space in need of correction. For instance, a suitable height of expansion may range from between about 1 mm to about 40 mm, for instance, about 5 mm and about 25 mm, such as about 6 mm and about 20 mm, including about 7 mm and about 15 mm, such as about 8 mm and about 10 mm.

Accordingly, in certain embodiments, as the distal end member moves along the extended retaining element, and the implant is expanded and the end member, or a portion thereof, contacts to a retaining member, or a portion thereof, and is thus prevented from moving away (e.g., horizontally) from the opposed, e.g., proximal, end member. In this manner, the retaining member is adapted for retaining the implant, once expanded, in the expanded configuration, and thus, the retaining member prevents the implant from contracting once expanded. Such "retaining" therefore may also be locking, that is, locking the implant in an expanded configuration.

In some embodiments, the retaining element comprises a first end associated with the first end of the implant, a second end associated with the second end of the implant, and a mechanical resistance element at one or both ends that substantially prevents the second end of the implant from moving away from the first end of the implant.

In some embodiments, the retaining element has an extended tubular body that is configured for moveably or non-moveably associating with one or more of the opposed end members. For instance, in one embodiment, the extended body of the retaining member may have a portion, such as a proximal portion, that includes an abutment portion, which abutment portion may be configured for preventing the substantial horizontal movement of the retaining member relative to the end member. Accordingly, in some instances, the abutment portion may be in any form so long as it is configured for contacting a proximal end member and adapted for preventing the passage of the retaining element through the end member. In such an embodiment, the abutment is configured for facilitating the association of the proximal portion of the retaining element with the end member. In some embodiments, the abutment portion may include a raised mating surface.

In some embodiments, the proximal and/or distal portions of the retaining element may include an abutment and/or a mating area with a mating surface, wherein the abutment and mating areas of the retaining element are configured for being associated with corresponding mating areas of end members and/or the apertures thereof. For instance, in some embodiments, a proximal or distal portion of a retaining element may include an abutment, wherein the abutment is configured for associating with an end member, for example, an exterior side of a proximal end member. In some embodiments, a proximal or distal portion of a retaining element may include a mating area, wherein the mating area is configured for associating with a corresponding mating surface of an end member, for example, a corresponding mating area of an aperture positioned within the end member. Such mating areas may be corresponding screw threads, and may also be a rivet-like configuration. In certain embodiments, neither the retaining element nor the end member(s) include corresponding mating surfaces that include screw-threads and/or rivet configurations, or the like.

In certain instances, an end member may include a configuration adapted to allow the end member to interact with the retaining member so as to facilitate the ability of the retaining member to prevent the expansible implant from contracting once it has been expanded. Accordingly, in certain embodiments, expansion of the implant may be coincident with the movement of an end member over one or more engagement member receiving elements of the retaining element, which function to prevent the implant from collapsing once expanded where one or a plurality of engagement member receiving elements are included, the degree of expansion can be modulated by the movement of an end member over one of the one or more of the engagement member receiving elements (i.e., movement over and relative to the retaining element).

Aperture

In some embodiments, the disclosed implant includes an extended retaining element, which retaining element is configured for being associated with the first 20 and second 21 opposed end members. In some embodiments, the first and second opposed end members may include an aperture, such as an aperture that extending through the end member. The aperture may be configured for receiving a retaining element. The retaining element may, therefore, be moveably and/or re-movably associated with one or more of the end members.

For example, the distal end member 21 may include an aperture that extends entirely from a front surface to a back surface of the end member through which a portion of the extended retaining element may entirely pass. The proximal end member 20 may also include an aperture that extends entirely through the length of the end member. The aperture may be such that it is configured for receiving an extended retaining element 200.

In some embodiments, the first end member 20 may form an abutment such that the extended retaining element may be passed entirely through the first end member, and extend toward and into the second end member. In this manner, as the distal end member is moved horizontally, e.g., in the x direction, toward the proximal the implant itself transitions from a collapsed or contracted configuration to an expanded configuration.

In certain embodiments, the first and second opposed end members may include a distal end member and a proximal end member, wherein the opposed end members are separated from one another by a distance d. In certain embodiments, at least one of the end members, e.g., the distal end member, includes an aperture configured for receiving at least a portion of the extended retaining element, and the other end member, e.g., the proximal end member, includes an abutment configured for receiving an end portion of the extended retaining element, once the extended element has been inserted through the aperture of the distal end member. In certain instances, the distal end member may be moveably associated with the extended retaining element such that the first, e.g., distal, end member may be capable of moving horizontally along the extended retaining member toward the second, e.g., proximal, end member thereby shortening the distance d between the two end members. In certain embodiments, as the second end 21 member moves along the extended retaining element, toward the first end member 20, the implant is expanded.

Further, in one embodiment, the extended body of the retaining member may have a portion, such as a distal portion, that is configured for moveably associating with a distal end member. For instance, in certain embodiments, an end member, such as a distal end member, may be adapted for being fitted over the retaining element and configured for moving, e.g., sliding, in the horizontal direction (defined by an axis corresponding to the length of the extended body of the retaining member) toward the opposing end member, e.g., the proximal end member. In this manner, the distance d between the proximal and distal opposed end members may be modulated by the movement of one end member, e.g., a distal end member, horizontally along the length of the retaining element toward a second, opposed end member, e.g., a proximal end member.

An aperture of an end member may be of any suitable shape and of any suitable size, so long as it is configured so as to receive a retaining element and/or snugly fit a retaining element there through. Such apertures may include a mating surface that includes screw threads which correspond to screw threads or plurality of ridges and grooves of a retaining member.

Groove and Ridges

In certain embodiments, the retaining element/member includes a plurality of raised ridges and corresponding grooves which are configured to interlock with another corresponding member of the implant (e.g., engagement member or circlip) located at the distal end of the implant. In certain instances, the retaining member is configured for interacting in such a manner that as the implant is expanded, the plurality of ridges and corresponding grooves controls or prevents the implant from contracting once expanded.

In some embodiments, the implant may include a mechanical resistance element that is configured for preventing the expansible implant from contracting once it has been expanded. For instance, in certain embodiments, the retaining element may include a mechanical resistance adapted for locking and thereby retaining the implant, once expanded, in the expanded configuration. For example, in certain embodiments, the mechanical resistance may include a retaining element, which may include plurality of raised ridges and corresponding groove portions there between.

Specifically, in certain instances, the retaining element may be configured for interacting with at least one of the end members in such a manner that as the implant is expanded, at least a portion of the end member becomes associated with at least a portion of the retaining element, which association prevents the implant from contracting once expanded. For instance, in one exemplary embodiment, as a distal end member moves forwards along the extended retaining element toward the proximal end member, and the implant is expanded, the end member, contacts the noted portion of the retaining element and is thereby prevented from moving horizontally backwards away from the opposed, e.g., proximal end member. In this manner, the retaining element is adapted for retaining the implant, once expanded, in the expanded configuration, and thus the retaining element prevents the implant from contracting once expanded. Such "retaining," therefore may also be locking, that is, locking the implant in an expanded configuration.

In some embodiments, the retaining member may be configured with one or more ridges that extend outwards away from the outer surface of the retaining member.

In some embodiments, the retaining member may be configured with one or more grooves or notches that extend inwards away from the outer surface of the retaining member.

In some embodiments, the retaining member may include a plurality of ridges and grooves that spans at least a portion of the circumference of the retaining member. For example, the ridge may be a portion of the retaining member that extends outwardly away from the outer surface of the retaining member. The ridges and grooves may span, e.g., circumscribe, the entire circumference of a portion of the outer surface of the retaining element or may span one or more portions of the retaining member.

Lumen

In certain embodiments, the retaining member may be elongated, tubular, and may include a lumen 252 therein. For instance, the retaining member may include a tubular body with an outer surface and an inner surface, wherein the inner surface bounds a lumen or passage way. Accordingly, in some embodiments, the tubular body is configured for receiving and/or passing a fluid through the body of the retaining member. The retaining member may additionally include one or more apertures configured for allowing the egress of a fluid there through.

Hence, in certain instances, the retaining element is configured for delivering a fluid, such as a bone cement, through the expansible implant to a site of delivery. For example, in some embodiments, the distal portion of the extended body is configured for associating with an expander and/or fluid delivery device, wherein the expander is capable of both facilitating the expansion of the expansible implant and/or may further be capable of transmitting a fluid from a fluid reservoir to the interior of the retaining member and subsequently out through a delivery aperture, such as an aperture positioned at a proximal portion of the retaining member. One or more apertures may be included, wherein the apertures may be any suitable size, shape, and/or configuration as desired. They may be spaced regularly or randomly around the circumference of the tubular body of the retaining member.

Figure 17:
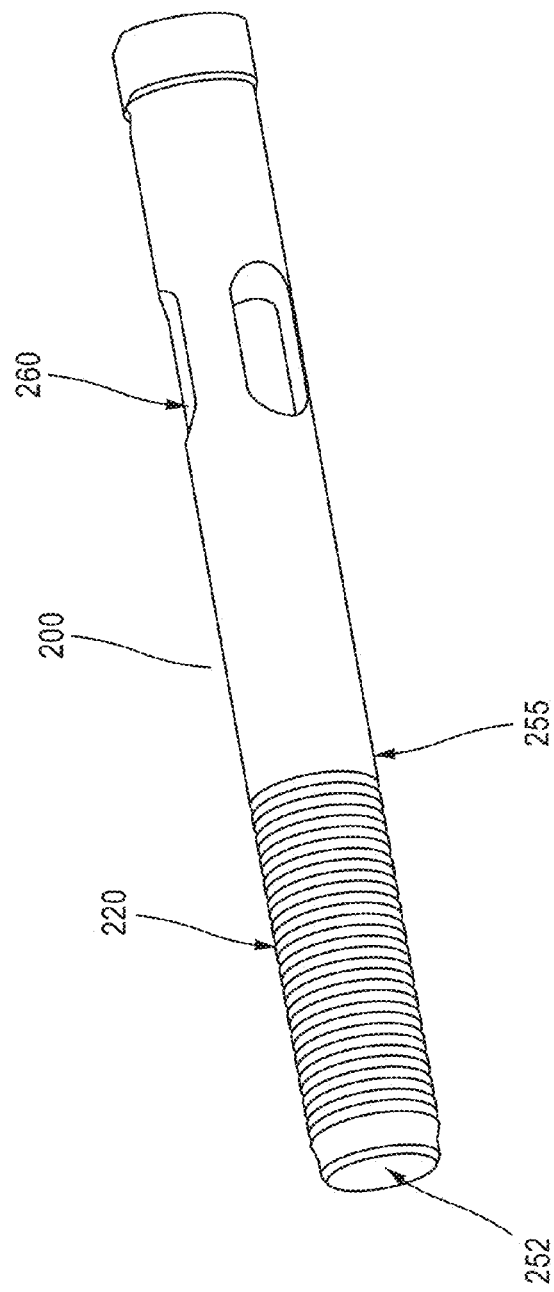
FIG. 17 illustrates a perspective view of an embodiment of a retaining element according to the disclosure.

FIG. 17 shows one embodiment of a retaining element 200, which retaining element includes a mechanical resistance. The retaining element 200 may include a plurality (e.g., one or more, such as 1, 2, 3, 4, 5, 6, 7, 8, p, etc) of an engagement member receiving element (e.g., blocking steps made up of a plurality of ridges and grooves) 220 and/or an egress aperture 260. The retaining element 200 may be an extended body that includes a passage 252 extending there through. The one or more apertures 260 may be configured for allowing the egress of a fluid that is passed through the passage 252 of the retaining element 200. As can be seen with reference to FIG. 17, the shape and configuration of the retaining element and mechanical resistance may vary. In FIG. 17, the retaining element 200 has a relatively smooth and planar outer surface that has a distal portion 255 that includes a plurality of engagement member receiving elements 220, which comprise a series of tube placement grooves and ridges.

In some embodiments, the lumen 252 of the retaining element 200 is designed to aid the diffusion of cement through the entire footprint of the implant. For example, cement is delivered via the lumen 252 of the retaining element 200 and spreads through the lumen 252 across the entire length (e.g., from proximal to distal side) of the retaining element, and in this manner is delivered to the distal end 21 of the implant and out of the lumen 252 to the distal side of the implant. Cement is delivered to points between the proximal 20 and distal 21 ends of the implant through one or more apertures 260 configured for allowing the egress of fluid cement there through. In this manner, cement fills the lumen 252 of the retaining element 200 and is delivered from one end of the implant to the other and to cavities there between (e.g., areas surrounding the implant within the vertebrae and/or cavities created by expansion of the implant).

Figure 18A:
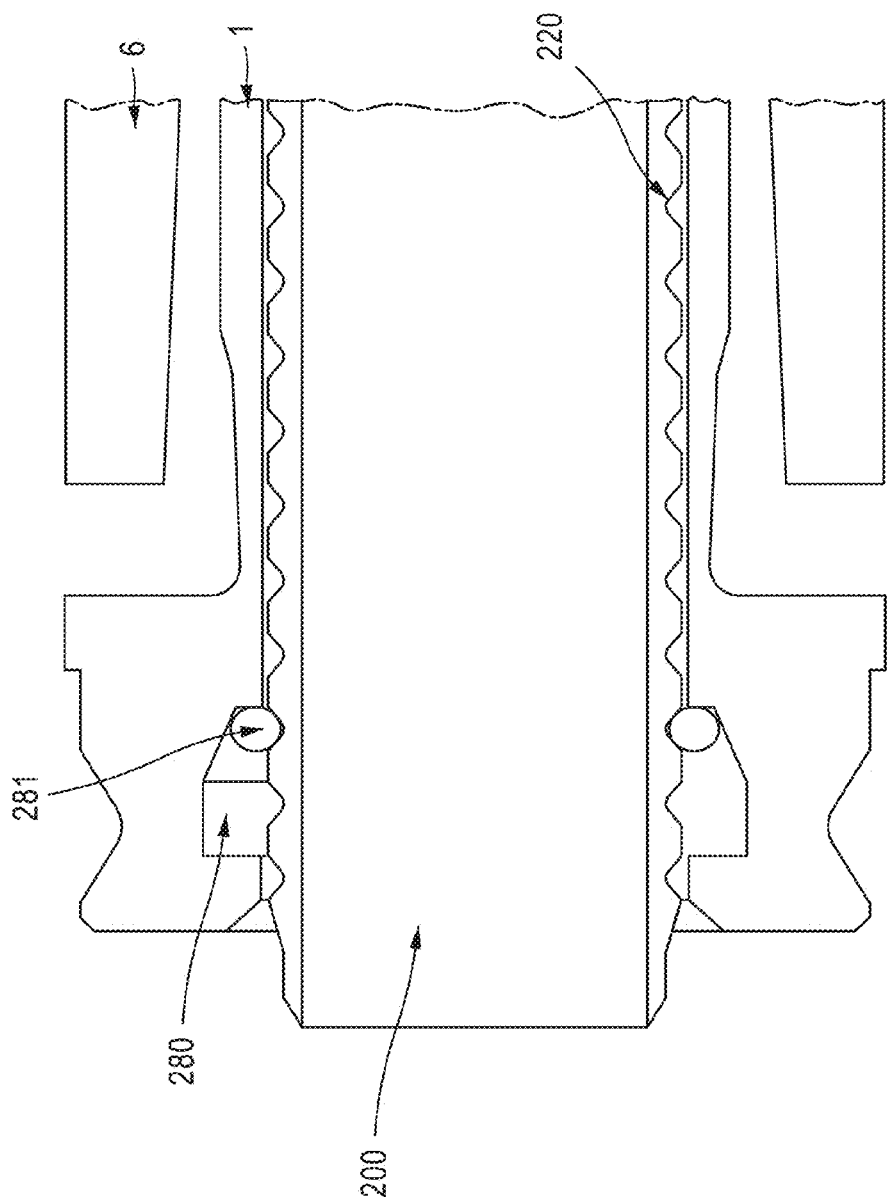
FIG. 18A illustrates a perspective view of an embodiment of an implant and a retaining element according to the disclosure utilizing a mechanical resistance having an implant groove area (or circlips room).
Figure 18D:
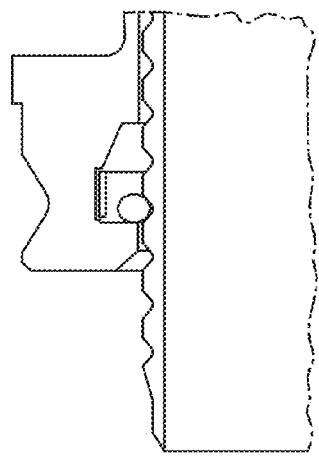
FIG. 18D. illustrates a perspective view of an embodiment of an implant and a retaining element and the placement of the circlip upon at the stop of contraction (the circlips fall back into a tube placement groove).
Figure 18C:
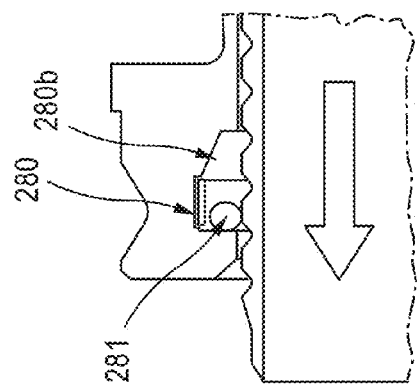
FIG. 18C. illustrates a perspective view of an embodiment of an implant and a retaining element and the placement of a circlip upon contraction of the implant.
Figure 18B:
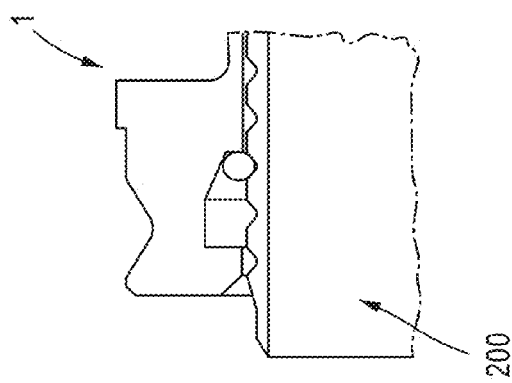
FIG. 18B. illustrates a perspective view of an embodiment of an implant and a retaining element according to the disclosure utilizing a mechanical resistance having an implant groove area (or circlips room) and circlip at an initial position.
Figure 18E:
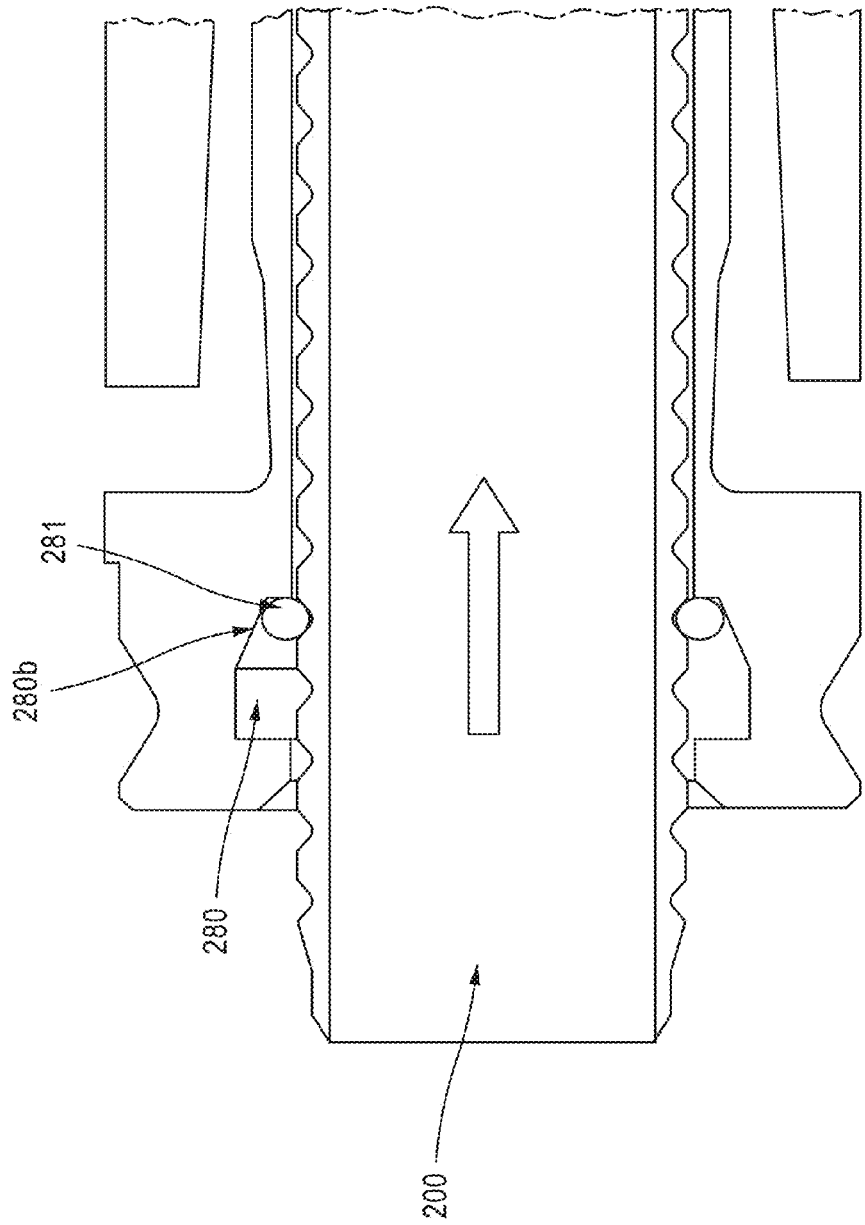
FIG. 18E. illustrates a perspective view of an embodiment of an implant and a retaining element and the placement of a circlip providing mechanical resistance to the movement of the retaining element.

FIGS. 18A to 18E illustrate the mechanical resistance of the retaining element 200 according to some embodiments. FIGS. 18B to 18D show a close up of the movement of one circlip as the implant 1 is contracted. FIG. 18B shows an initial position of the retaining member engagement member (e.g., circlip) 281, which is housed within an opening or recess 280 of an end member (20, 21). FIG. 18C shows the movement of the circlip during the expansion of the implant 1 (e.g., as end member 21 is moved toward end member 20 (not shown)). In this instance, the elastic circlip is pushed over the tube placement grooves and the ridges 220 and the circlip provides no mechanical resistance to the expansion of the implant 1. The free space 280a of the recess of the end member 280 allows the movement of the circlip 281 and passage of the retaining element 200.

When the contraction has ceased, the circlips fall back into the tube placement grooves. See FIG. 18D. When the implant is relaxed and the elastic return of the material and/or downward pressure on the implant 1 pulls the retaining element 200 tube in the opposite direction, the circlip 281 comes into contact with the surfaces of the blocking steps 220, which are configured to prevent movement of the retaining element 200 in the opposite direction. In the manner, the retaining wall or surface 280b or the recess 280 may be angled or tapered so as to eliminate the free space 280a and thus prevent to upward movement of the circlip 281 upon the attempted passage of a ridge of an engagement member receiving element 220. Thus, the circlips 281 are maintained in the groove of a blocking step 220 and block the translation of the retaining element 200. In this manner, increased compression is met with mechanical resistance once the implant 1 is open and free from the implant expander element. According, the retaining element 200 aids in maintaining height positioning of the implant 1, limit the elastic return (spring back effect) and/or decreases the distance between each blocking step 220.

The presence of the blocking steps 220 (ridges and tube placement grooves), may be used to stop the translation between the two end parts at varying lengths. One positioned, the retaining element 200 may be used to inject cement via the implant expander. This system blocks the horizontal translation of the implant 1 as well as fixes its height position.

The width of the ridge(s) of the blocking steps 220 may be between about 0.2 mm to about 2 mm, such as about 0.5 mm, 0.6 mm, 0.7 mm, 0.8 mm, 0.9 mm, 1 mm, 1.2 mm, 1.3 mm, 1.4 mm, 1.5 mm, 1.6 mm, 1.7 mm, 1.8 mm, 1.9 mm, or 2.0 mm). The width of the groove is configured to fit a circlip 281 that is housed in an implant groove area 280. See e.g., FIG. 18A. The width of the ridge(s) may vary for a single retaining element 200. For example, the width of the ridge(s) may be reduced with the increased expansion of the implant 1.

According to some embodiments, the implant expander may allow for the transfer of cement directly inside the implant. For example, in a first step, the implant expander deploys the implant and in a second step, the expandable part will be removed and the retaining element 200 or tube will remain in place, which can then be used to drive the injection system.

Definitions

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the disclosure will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present disclosure. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth.

Throughout this application, the term "about" is used to indicate that a value includes the standard deviation of error for the device or method being employed to determine the value.

Reference to numeric ranges throughout this specification encompasses all numbers falling within the disclosed ranges. Thus, for example, the recitation of the range of about 1% to about 5% includes 1%, 2%, 3%, 4%, and 5%, as well as, for example, 2.3%, 3.9%, 4.5%, etc.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any and all references to publications or other documents, including but not limited to, patents, patent applications, articles, webpages, books, etc., presented in the present application, are herein incorporated by reference in their entirety.

Although a few variations have been described in detail above, other modifications are possible. The particular embodiments disclosed herein in detail is provided by way of example and purposes of illustration only, and is not intended to be limiting with respect to the scope of the appended claims, which follow. In particular, it is contemplated that various substitutions, alterations, and modifications may be made without departing from the spirit and scope of the invention as defined by the exemplary claims. Other aspects, advantages, and modifications are considered to be within the scope of the following exemplary claims. The exemplary claims presented are representative of only some of the embodiments and features disclosed herein. Other unclaimed embodiments, inventions, and features are also contemplated.

What is claimed is:

1. A vertebral expandable implant, comprising:
    at least one bearing surface which expands away from a central longitudinal axis of the implant;
    a first implant end and an opposed second implant end, wherein at least one of the first implant end and the opposed second implant end includes an opening or retaining recess, and wherein the first implant end and the opposed second implant end are intended to move toward one another during expansion of the implant;
    a retaining member comprising an elongate structure having a first retaining member end and a second retaining member end, wherein at least one of the first retaining member end and the second retaining member end is configured to engage with a respective opening or retaining recess of the first implant end and the opposed second implant end, and wherein at least one retaining member end comprises a plurality of ridges of varying widths and corresponding plurality of grooves therebetween; and
    at least one retaining member engagement element provided within the opening or retaining recess of the at least one of the first implant end and the opposed second implant end, wherein the at least one retaining member engagement element is configured to engage a single groove of the plurality of grooves at a time; wherein the opening or retaining recess of the at least one of the first implant end and the opposed second implant end comprises:

a first opening or retaining recess end having sufficient depth to allow passage of the engagement element when the engagement element is positioned on a ridge of the plurality of ridges, and a second opening or retaining recess end lacking sufficient depth to allow passage of the engagement element when the engagement element is positioned on a ridge of the plurality of ridges; and the retaining member is configured for retaining the expandable implant in an expanded configuration by substantially preventing contraction of the expandable implant when expanded.

2. The expandable implant according to claim 1, wherein the plurality of ridges and the plurality of grooves at least partially circumscribe an outer surface of the retaining member.

3. The expandable implant according to claim 1, wherein the plurality of ridges and the plurality of grooves completely circumscribe a circumference of an outer surface of the retaining member.

4. The expandable implant according to claim 1, wherein the plurality of grooves extend inward away from an outer surface of the retaining member, wherein upon expansion of the implant, the at least one retaining member engagement element moves between ridges and grooves during the passage of the retaining member.

5. The expandable implant according to claim 1, wherein the retaining member is tubular and the plurality of ridges and the plurality of grooves at least partially circumscribe an outer surface of the retaining member.

6. The expandable implant according to claim 1, wherein the retaining member is tubular and comprises a lumen configured for allowing passage of a flowable material therethrough.

7. The expandable implant according to claim 6, wherein the retaining member further comprises an aperture configured for allowing an egress of the flowable material from the lumen of the tubular retaining member.

8. The expandable implant according to claim 7, wherein the flowable material comprises a bone cement or bone graft.

9. The expandable implant according to claim 1, wherein at least one of the first implant end and the opposed second implant end is configured for association with an implant expander.

10. The expandable implant according to claim 9, wherein the implant expander comprises a proximal portion and a distal portion, wherein the distal portion is configured for association with at least one of the first implant end and the opposed second implant end.

11. The expandable implant according to claim 10, wherein the proximal portion of the implant expander is configured for being coupled to an injection member of an injection system.

12. The expandable implant according to claim 11, wherein the proximal portion comprises a luer lock, threaded, or bayonet configuration.

13. The expandable implant according to claim 1, wherein expansion of the implant comprises movement of at least one of the first implant end and an opposed second implant end relative to the retaining element member.

14. The expandable implant according to claim 1, wherein the at least one retaining member engagement element is a circlip.

15. The implant according to claim 1, wherein the varying widths of the plurality of ridges are reduced with increased expansion of the implant.

16. A method for retaining an expandable implant in an expanded condition, the said method comprising:

introducing into a bone an expansible implant, said implant comprising:

at least one bearing surface which expands away from a central longitudinal axis of the implant, and a first implant end and an opposed second implant end, wherein the first implant end and the opposed second implant end are intended to move toward one another during expansion of the implant, and wherein at least one of the first implant end and the opposed second implant end includes an opening or retaining recess, said opening or retaining recess housing at least one engagement element;

expanding the implant such that the implant engages a mechanical resistance configured to prevent a compression of the implant, wherein:

said mechanical resistance is placed between the first implant end and the opposed second implant end, and said mechanical resistance includes a retaining member comprising an elongate structure having a first retaining member end and a second retaining member end, wherein at least one of the first retaining member end and the second retaining member end comprises a plurality of ridges of varying widths and corresponding plurality of grooves therebetween, and wherein the at least one of the first retaining member end and the second retaining member end is configured to engage a respective opening or retaining recess of the first implant end and the opposed second implant end; and positioning the retaining member such that the at least one engagement element engages a single groove of the plurality of grooves at a time;

wherein the opening or retaining recess is configured to permit passage of the at least one engagement element over the plurality of ridges during expansion on the implant, and wherein the opening or retaining recess is configured to block passage of the at least one engagement element over a ridge of the plurality of ridges upon application of a compression force to the implant, thereby retaining the at least one engagement element in a groove of the plurality of grooves, and thereby retaining the implant in an expanded configuration by substantially preventing contraction of the implant when expanded.

17. The method according to claim 16, wherein the plurality of ridges and the plurality of grooves at least partially circumscribe an outer surface of the retaining member.

18. The method according to claim 16, wherein the plurality of ridges and the plurality of grooves completely circumscribe a circumference of an outer surface of the retaining member.

19. The method according to claim 16, wherein the plurality of grooves extend inward away from an outer surface of the retaining member, wherein upon expansion of the implant, the at least one engagement element moves between ridges and grooves during the passage of the retaining member.

20. The method according to claim 16, wherein the retaining member is tubular and the plurality of ridges and the plurality of grooves at least partially circumscribe an outer surface of the retaining member.

21. The method according to claim 16, wherein the retaining member is tubular and comprises a lumen configured for allowing passage of a flowable material therethrough.

22. The method according to claim 21, wherein the retaining member further comprises an aperture configured for allowing an egress of the flowable material from the lumen of the tubular retaining member.

23. The method of claim 21, wherein the flowable material comprises a bone cement or bone graft.

24. The method according to claim 16, wherein at least one of the first implant end and the opposed second implant end is configured for association with an implant expander.

25. The method according to claim 24, wherein the implant expander comprises a proximal portion and a distal portion, wherein the distal portion is configured for association with at least one of the first implant end and the opposed second implant end.

26. The method according to claim 25, wherein the proximal portion of the implant expander is configured for being coupled to an injection member of an injection system.

27. The method according to claim 26, wherein the proximal portion comprises a luer lock, threaded, or bayonet configuration.

28. The method according to claim 16, wherein expansion of the implant comprises movement of at least one of the first implant end and the opposed second implant end relative to the retaining member.

29. The method according to claim 16, wherein the varying widths of the plurality of ridges are reduced with increased expansion of the implant.

\* \* \* \* \*